United States Patent [19]

Schorr et al.

[11] Patent Number: 4,692,523
[45] Date of Patent: Sep. 8, 1987

[54] PROCESS FOR THE PREPARATION OF 1-SUBSTITUTED AZA-CYCLOALKAN-2-ONES

[75] Inventors: Manfred Schorr, Frankfurt am Main; Wilfried Schmitt, Kelkheim, both of Fed. Rep. of Germany

[73] Assignee: Hoechst Aktiengesellschaft, Frankfurt, Fed. Rep. of Germany

[21] Appl. No.: 916,373

[22] Filed: Oct. 7, 1986

[30] Foreign Application Priority Data

Oct. 9, 1985 [DE] Fed. Rep. of Germany ....... 3536028

[51] Int. Cl.$^4$ ................ C07D 207/267; C07D 211/76; C07D 223/10; C07D 225/02
[52] U.S. Cl. .................................... 540/533; 540/451; 540/485; 546/243; 548/543; 548/552
[58] Field of Search ....................... 540/451, 485, 533; 546/243; 548/543, 552

[56] References Cited

U.S. PATENT DOCUMENTS 3,332,938  7/1967  Mayhew et al. .................... 540/485
3,865,814  2/1975  Lussi et al. ......................... 540/533

OTHER PUBLICATIONS

Leonhard Birkofer et al., Chem. Ber. 102, 3094–3101 (1969).

*Primary Examiner*—Robert T. Bond
*Attorney, Agent, or Firm*—Finnegan, Henderson, Farabow, Garrett & Dunner

[57] ABSTRACT

A process for the preparation of 1-substituted azacycloalkan-2-ones of the formula I

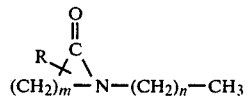

in which R, m and n have the meanings indicated by reaction of corresponding 1-trimethylsilylazacycloalkan-2-ones with alkali metal alcoholate or alkali metal oxide and then alkylation of the alkali metal salts which are formed.

3 Claims, No Drawings

PROCESS FOR THE PREPARATION OF 1-SUBSTITUTED AZA-CYCLOALKAN-2-ONES

It is known that 1-substituted azacycloalkan-2-ones of the general formula I

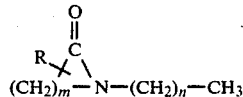

in which R denotes hydrogen or lower alkyl having 1–4 carbon atoms, m denotes 3–7, and n denotes 0–17, increase the ability of pharmaceutically active compounds to penetrate through the skin. Thus, there are descriptions in U.S. Pat. Nos. 3,989,816, 4,316,893 and 4,405,616 of pharmaceutical formulations which, as a consequence of their content of compounds of the formula I, are suitable for the transdermal administration of medicaments. Furthermore, it is shown in U.S. Pat. No. 4,311,481 that 1-substituted azacycloalkan-2-ones of the indicated structure promote the penetration of dyes into textile fibers and thus improve the dyeing process.

Compounds of the general formula I are generally prepared by alkylation of 1-unsubstituted azacycloalkan-2-ones of the general formula II

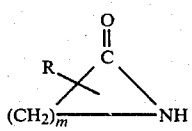

in which R and m have the above-mentioned meaning, by the action of an alkylating agent such as, for example, an alkyl halide or an alkyl sulfonate. This entails the necessity for the azacycloalkan-2-one to be converted into its anion beforehand. This is achieved by reaction with metallic sodium (Helv. Chim. Acta 4 (1921), 480) or sdium hydride or sodamide (U.S. Pat. No. 4,316,893). Use of these reagents demands, because of their high reactivity, particularly to moisture, special precautionary and protective measures, for which reason the operations, preferably on the industrial scale, take a difficult and elaborate form.

There is a description in Chem. Ber. 102, (1969), 3094, that sodium salts of carboxamides can be obtained by allowing sodium silanolate to act on the corresponding N-trimethylsilyl derivatives. The especially high bond energy of the silicon-oxygen bond in disiloxanes results in the formation of hexamethyldisiloxane with simultaneous production of the sodium salt of the amide. However, this simple process is restricted to use on the laboratory scale. The difficulty of obtaining, and the resulting high price of, sodium silanolate prevents its use in industrial processes.

It has now been found, surprisingly, that 1-substituted azacycloalkan-2-ones of the general formula I can be prepared in a simple manner by the corresponding 1-trimethylsilyl compounds being reacted with alkali metal alcoholate or alkali metal oxide and then alkylated.

Hence the invention relates to a process for the preparation of the compounds of the formula I

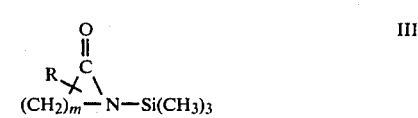

in which R, m and n have the meanings indicated, which comprises 1-trimethylsilylazacycloalkan-2-ones of the general formula III $$\underset{(CH_2)_m - N - Si(CH_3)_3}{\overset{O}{\underset{\|}{R \diagdown C \diagdown}}} \quad III$$

in which R and m have the above-mentioned meanings, being reacted with an alkali metal alcoholate or an alkali metal oxide and, for the introduction of the alkyl radical —(CH$_2$)$_n$CH$_3$, an alkylating agent being allowed to act in a manner known per se on the alkali metal salt of the azacycloalkan-2-one which has formed. This does not entail the necessity to isolate the alkali metal salt, so that the reaction can be carried out continuously in one vessel.

The N-trimethylsilylazacycloalkan-2-ones used as starting material can be prepared in a simple and low-cost manner from the unsubstituted azacycloalkan-2-ones of the general formula II by reaction with trimethylchlorosilane in the presence of triethylamine (Chem. Ber. 99, 3820 (1966)) or with hexamethyldisilazane (European Pat. No. A-0,043,630).

Alkali metal alcoholates or alkali metal oxides which are used in the first step and which are suitable and preferred are the alcoholates or oxides of lithium, sodium or potassium. It is particularly advantageous to use sodium methylate, sodium ethylate or sodium oxide. These reagents, which are readily accessible and low-cost, can be manipulated even on the industrial scale without hazard and without additional elaboration and special precautionary measures.

The reactions are advantageously carried out in the presence of an inert solvent. Aromatic hydrocarbons such as, for example, benzene or toluene, or aliphatic or aromatic ethers, such as, for example, 1,2-dimethoxyethane or anisole, are particularly suitable.

The reaction is expediently carried out in such a manner that first the alkali metal alcoholate or oxide is suspended in the inert solvent, and then the 1-trimethylsilylazacycloalkan-2-one, where appropriate dissolved in the same solvent, is added. The formation of the in alkali metal salt of the azacycloalkan-2-one takes place even at room temperature. However, to increase the rate of and complete the reaction, it is frequently advantageous to heat to higher temperatures, for example to the boiling point of the solvent used.

The alkylating agent is then added to the reaction mixture, where appropriate after cooling beforehand. Suitable alkylating agents are alkyl halides or esters of alcohols with sulfuric acid or aliphatic or aromatic sulfonic acids. The reaction with the sodium salt can take place even at room temperature. However, in general it is advantageous to operate at elevated temperature, preferably between 50° and 150° C.

After the reaction is complete, the alkali metal compound which has formed, such as an alkali metal halide or sulfonate, is removed by filtration, and the solvent is removed by distillation. In general, the 1-substituted azacycloalkan-2-ones remain behind as oils and can be obtained in the pure form by distillation in vacuo.

However, the reaction mixture can also be worked up in such a manner that first the solvent is removed by distillation in vacuo, the residue is treated with water and with a water-immiscible solvent, and the latter is removed, dried and evaporated. The remaining oil is then distilled in vacuo.

EXAMPLE 1

N-n-dodecylcaprolactam 37 g (0.2 mol) of N-trimethylsilylcaprolactam are added dropwise to a suspension of 10.8 g (0.2 mol) of sodium methylate in 300 ml of toluene at room temperature, and the mixture is stirred for a further 30 minutes. This results in the formation of a thick suspension of the sodium salt of the caprolactam. After addition of 49.8 g (0.2 mol) of n-dodecyl bromide, the reaction mixture is stirred and heated under reflux for 20 hours. The toluene is then removed by distillation in vacuo, the residue is taken up with diethyl ether and water, and the ether phase is separated off, washed four times with water, and dried over sodium sulfate. After the ether has been removed by distillation, the remaining oil is distilled in vacuo.

Boiling point (0.17 mm) 182°–184° C.; yield 39.7 g.

EXAMPLE 2

N-n-dodecylcaprolactam

Reaction analogous to Example 1; 300 ml of 1,2-dimethoxyethane are used as solvent in place of 300 ml of toluene.

Boiling point (0.15 mm) 175°–176° C.; yield 39.5 g.

EXAMPLE 3

N-n-dodecylcaprolactam 3.1 g (0.05 mol) of sodium oxide ($Na_2O$) are suspended in 150 ml of 1,2-dimethoxyethane, and then 18.5 g (0.1 mol) of N-trimethylsilylcaprolactam are added. The reaction mixture is stirred at 50° C. for two hours, during which the voluminous precipitate of the sodium salt of the caprolactam forms. Then 24.9 g (0.1 mol) of n-dodecyl bromide are added, and the mixture is stirred and heated under reflux for 20 hours. The working-up is carried out as indicated in Example 1.

Boiling point (0.15 mm) 175°–176° C.; yield 20.8 g.

EXAMPLE 4

N-methylcaprolactam 5.4 g (0.1 mol) of sodium methylate and 18.5 g (0.1 mol) of N-trimethylsilylcaprolactam are introduced successively into 150 ml of 1,2-dimethoxyethane, and the mixture is stirred at room temperature for 30 minutes. Then 11 g (0.1 mol) of methyl methanesulfonate are added dropwise. After the reaction mixture has been stirred at 50° C. for a further one hour, it is cooled, the sodium mesylate is removed by filtration with suction, and the filtrate is evaporated. The oily residue is distilled in vacuo.

Boiling point (6 mm) 100°–102° C.; yield 8.9 g.

EXAMPLE 5

1-n-hexylpyrrolidin-2-one 31.4 g (0.2 mol) of 1-trimethylsilylpyrrolidin-2-one are added rapidly to a suspension of 10.8 g (0.2 mol) of sodium methylate in 200 ml of 1,2-dimethoxyethane. The reaction mixture is heated under reflux for a further 2 hours to complete the reaction, then cooled, and 31 g (0.2 mol) of n-hexyl bromide are added dropwise. The mixture is then heated under reflux for 8 hours, cooled, and the resulting sodium bromide is removed by filtration with suction. After the filtrate has been evaporated, the remaining oil is distilled in vacuo.

Boiling point (0.35 mm) 91°–93° C.; yield 26 g.

What is claimed is:

1. A process for the preparation of 1-substituted azacycloalkan-2-ones of the formula I

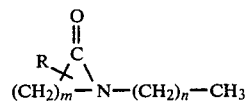

in which R denotes hydrogen or lower alkyl having 1–4 carbon atoms, m denotes 3–7 and n denotes 0–17, which comprises reacting a 1-trimethylsilylazacycloalkan-2-one of the formula III

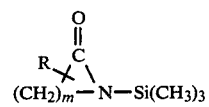

in which R and m have the above-mentioned meanings with an alkali metal alcoholate or an alkali metal oxide and, for the introduction of the alkyl radical —$(CH_2)_nCH_3$, reacting the alkali metal salt of the azacycloalkan-2-one thus formed with an alkylating agent.

2. The process as claimed in claim 1, wherein sodium methylate or sodium ethylate is used as the alkali metal alcoholate.

3. The process as claimed in claim 1, wherein sodium oxide is used as the alkali metal oxide.

* * * * *